Jan. 15, 1957 T. E. MOTOSE Plant Pat. 1,552
ROSE PLANT
Filed Jan. 27, 1956
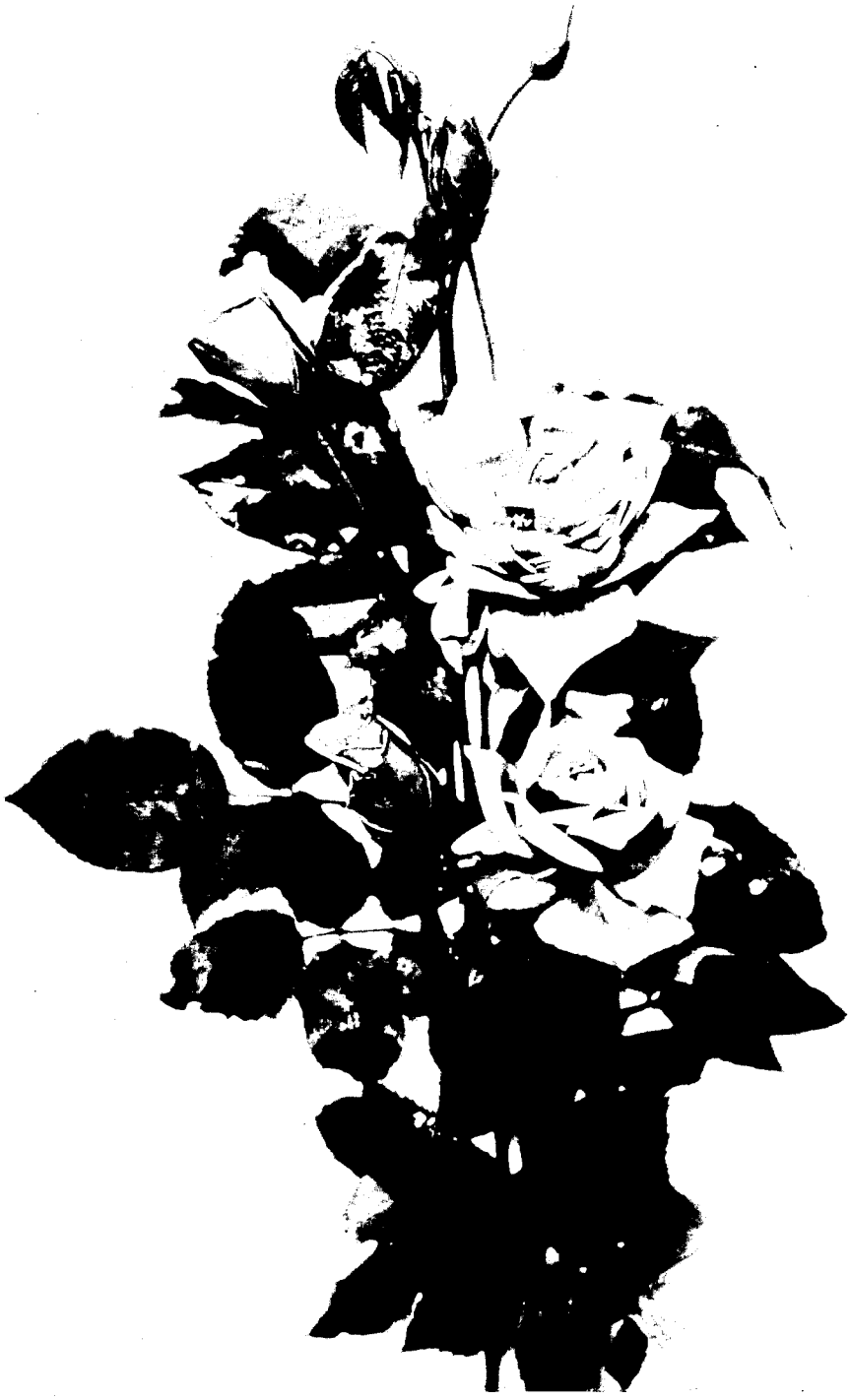
Inventor Thomas Edison Motose United States Patent Office Plant Pat. 1,552
Patented Jan. 15, 1957

1,552

ROSE PLANT

Thomas Edison Motose, Fairport, N. Y.

Application January 27, 1956, Serial No. 561,956

1 Claim. (Cl. 47—61)

This invention relates to a new and distinct variety of plant of the genus Rosa originating as a cross of the known variety Capistrano (Plant Patent No. 922) and a seedling which was an unnamed cross of the known varieties Mme. A. Meilland (Plant Patent No. 591) and Crimson Glory (Plant Patent No. 105).

In making the crosses, I had for my object the production of a rose possessing a sweet fragrance of great intensity and a combination of several colors different from those of other varieties. After numerous trials the objective was attained in the cross described in the preceding paragraph.

*The distinguishing characteristics*

This new variety possesses the following distinguishing characteristics:

(*a*) A sweet fragrance of great intensity which may be described as that coming from a dish filled with ripe red raspberries, slightly crushed, and covered with amber colored honey. (NOTE.—This reasonably accurate and most practical description is used because of the lack of generally acceptable technical nomenclature or "standard" in identifying and describing odors.)

(*b*) An unusual combination of colors in its blooms; outer or under surface of larger petals colored Tyrian Rose (Plate No. XII) when flower is half blown or Rose Color (Plate No. XII) when fully opened and well marked with "Veins" of slightly darker shade, inner or upper surface of the medium and small petals (and occasionally the larger ones too) colored Capucine Buff (Plate No. III) and various shades of amber overcast with light pink;

(*c*) Glossy, Forest Green (Plate No. XVII) mature leaves sharply serrated leaflets tending to crinkle slightly on both sides;

(*d*) Well branched, tall bush, attaining a height of five or more feet at maturity when grown outdoors in ordinary garden soil;

(*e*) Abundant production of fragrant blooms almost endlessly during growing seasons;

(*f*) Greater resistance to black spots and mildew than its parental varieties as shown in tests conducted in outdoor garden in Fairport, N. Y.;

(*g*) Great hardiness equal to that of wild roses as shown by its ability to survive the northern winter of the United States without the customary winter protection given to other hybrid tea roses; and lastly, but not the least, (*h*) Great ease in asexual reproductions—easily rooted, budded or grafted.

The three named ancestors of this new variety are all distinct varieties and are so recognized wherever they are grown. The combination of the above listed characteristics is not found in any one of the said three varieties, nor in the unnamed pollen parent. The general pattern, combination of colors and fragrance of the new variety are easily distinguishable from those of the parents and other varieties by an average person. The combination of the above characteristics, embodied in this new variety, makes this variety different from the parental, ancestral and other known varieties.

The above described characteristics and the combination thereof of this new variety have been found to be established definitely and to hold true through succeeding asexual reproductions. Buddings, cuttings, layerages and graftings of the new variety, performed in Fairport, N. Y., have always confirmed the fact that said characteristics and the combination thereof are transmissible asexually.

The accompanying picture of this new variety shows the shape, relative size and colors of its various parts, as seen in the early morning hours on a bright day early in September. There is little or no differentiating features in the very young leaves, immature buds and very old blooms, and no special effort has been made to illustrate or color them in detail other than those appearing incidentally in the picture.

The place where, and the time when, observations made for the specific purpose of compiling data for this specification: Fairport, N. Y., first week in September, 1955.

The following is a detailed description of this new variety of rose plant, with color terminology in accordance with Ridgway's Color Standard and Nomenclature (when plate number is given with color name) or accordance with the generally accepted meaning of Webster's standard dictionary (when plate number is not given):

(*1*) *Parentage*

A seedling originated as a cross of Capistrano (seed parent) and an unnamed seedling (pollen parent), the latter being a cross of Mme. A. Meilland and Crimson Glory.

(*2*) *Classification*

*Botanic.*—A shrub or woody perennial plant belonging to the continuous or recurrent blooming hybrid varieties of the cultivated species of the genus Rosa.

*Commercial.*—A bush-type hybrid-tea rose plant.

(*3*) *Plant as a whole*

*Form.*—Bushy and well branched.

*Growth.*—Very vigorous and fast growing.

*Height at maturity.*—Tall; five or more feet in outdoor gardens as observed in Fairport, N. Y.

(*4*) *Canes and stems*

*Very young canes.*—Smooth bark, Oil Green (Plate No. 5) overcast with Brick Red (Plate No. 13).

*Young canes.*—Smooth bark, Peacock Green (Plate No. 6) slightly overcast with light pink.

*Mature or near mature canes.*—Spinach Green (Plate No. 5).

*Very old canes.*—Spinach Green (Plate No. 5) with brown colored streaks.

(*5*) *Foliages*

*Quantity.*—Abundant.

*Composition.*—Five leaflets to an average leaf, rarely three or seven.

*Size.*—Large.

*Shape of leaflet.*—Oval, but pointed on both ends as a rule—the free end pointed much more than the other end; slightly crinkled or waved on both sides (meaning left and right and not obverse and reverse).

*Texture and appearance.*—Reverse side being leathery and obverse side smooth and glossy when young; reverse side leathery and obverse side just smooth when old.

*Serration.*—Conspicuous, multiple.

*Ribs and veins.*—Conspicuous and clearly marked.

*Color.*—Both sides of very young leaves—very light green with a heavy overcast of Brick Red (Plate No. 13); upper side of young leaves—Oil Green (Plate No. 5) with a slight overcast of Brick Red (Plate No. 13); underside of young leaves—Yellowish Oil Green (Plate No. 5) with a slight overcast of Brick Red (Plate No. 13); upper side of mature leaves—Forest Green (Plate 17) and often Spinach Green (Plate No. 5) in warm weather; under side of mature leaves—light green and often Light Bice Green (Plate 17).

*Leaf stem.*—Bice Green (Plate 17) in color.

*Stipules.*—Light Bice Green (Plate 17) in color.

(6) *Flower buds*

*Size.*—*Large.*

*Shape.*—Ovoid base and pointed upper tip.

*Sepals.*—Not serrated and not branched as a rule; Calliste Green (Plate No. 6) inside and Scheele's Green (Plate No. 6) outside; one and half to two inches long.

*Calyx.*—Medium to large in size; ovoid, but more pointed at the base than any of those of the parent varities; Scheele's Green, Plate No. 6) and often a shade darker in coloring.

*Peduncle.*—Medium in length; medium in diameter; slightly rough; strong; Scheele's Green (Plate No. 6).

*Color of visible parts of petal.*—Tyrian Rose (Plate No. 12) when sepals first divide; Tyrian Rose (Plate No. 12) towards the base, Rose Color (Plate No. 12) towards the top, Capucine Buff (Plate No. 3) and various shades of amber (frequently overcast with light pink) on the top edges and inner surface of petals when half blown.

(7) *Flowers*

*Opening.*—Opens up well in most weather conditions.

*Life span of bloom.*—About the same as that of hybrid tea rose named "Better Times."

*Size.*—Large, about five inches in diameter when fully opened in outdoor garden, about six inches in diameter when fully opened under greenhouse protection.

*Borne.*—Singly as a rule.

*Form.*—High centered during most of its blooming stages, saucer-shape just before scattering or falling of petals.

*Colors of bloom when about half to three-fourths opened as viewed from above.*—Capucine Buff (Plate No. 3) on the free edges and visible parts of inner surface of large petals; various shades of amber (frequently overcast with light pink) on the inner or upper surface of medium and small petals; Rose Color (Plate 12) on the visible parts of the under or outside surface of all the petals.

*Colors of bloom when one-half to three-fourths open when viewed from below.*—Base and mid-section colored Tyrian Rose (Plate No. 12) or very closely related color, which gradually becomes Rose Color (Plate No. 12) outward and upward; occasionally the color Capucine Buff (Plate No. 3) is visible whenever the petals curl back.

*Colors of bloom when fully opened but still fresh as viewed from above.*—Outer area (larger petals) colored Rose Color (Plate No. 12) with exception noted below; next to the outer area colored Capucine Buff (Plate No. 3) overcast with light pink; inner area colored in various shades of amber, lightly overcast with pink; scattered on all areas wherever the curvature or the position of petals reveal the reverse side—Rose Color (Plate No. 12). The outer and the next to the outer areas are very frequently all Capucine Buff (Plate 3) overcast with pink and without a solid area of Rose Color (Plate 12) in cool weather or when grown under glass.

*Colors of bloom when fully opened but still fresh as viewed from below.*—Rose Color (Plate No. 12) with Capucine Buff (Plate 23) edges where the free sides of petals curl back.

*Color of the base of bloom when sepals have curled back sufficiently.*—Maize Yellow (Plate No. 4) lightly overcast with pink; often just plain yellow.

*General color as viewed from about 25 feet in good daylight during the first two days of bloom.*—Rose Color (Plate No. 12) with buff or amber top and center, and clearly distinguishable from other roses growing side by side.

*General coloring at the end of fifth day of blooming.*—Top and central areas colored with very light buff or pale amber, overcast with light pink; outer surface of all the petals (and the inner surface of larger petals during warm season) colored light pink with a very light overcast of buff. (Coloring at this late stage is transitory and variable and is difficult to be described specifically with plate number.)

*Fragrance.*—Resembling the fragrance coming from a dish of ripe red raspberries, slightly crushed and covered with amber colored honey, and occasionally a very slight addition of tea scent.

(8) *Petals*

*Shape of large outer petals.*—Ovate with the narrow end at the base.

*Shape of medium and small petals.*—Ovate with the narrow end as the base.

*Arrangement.*—Irregular.

*Persistence.*—Clings during wet season, drops off cleanly in dry weather.

*Thickness.*—*Thin.*

*Veins.*—Well marked—conspicuous.

*Appearance.*—Both sides satiny.

*Texture.*—Smooth.

*Size of outer petals.*—About two and half inches long and about two inches wide near the top.

*Color of upper or inner surface of outer petals when fully unfurled or during the first few days of bloom.*—Rose Color (Plate No. 12) in hot weather; Capucine Buff (Plate No. 3) overcast with light pink in cool weather or when grown under glass any season; Capucine Buff (Plate No. 3) and Rose Color (Plate No. 12) occupying the various parts of the same side of petals during the transition period from hot to cool.

*Color of upper or inner surface of intermediate and small petals when fully unfurled or during the first few days of bloom.*—Capucine Buff (Plate No. 3) and various shades of amber, all overcast with light pink, hot or cool season, indoors or outdoors.

*Color or outer or under surface of all the petals when bloom is still fresh or during the first few days when fully unfurled.*—Rose Color (Plate No. 12) or closely related color (all seasons, indoors or outdoors).

*Color of base of petals.*—Maize Yellow (Plate No. 4); frequently just plain light yellow.

*Color of the visible part of partly unfurled petals.*—Tyrian Rose (Plate No. 12) under or outerside, and Capucine Buff overcast with light pink upper or inner side.

*Number of petals on an average bloom.*—About 35 in Summer; 45 or more in cool seasons.

(9) *Thorns*

*Size.*—Medium.

*Quantity.*—Ordinary.

*Shape.*—Wide base (with the free end pointed straight outward in right angle to the cane as a general rule).

*Color.*—Various shades of brown when old; light pink when young.

(10) *Genital organs*

*Anthers.*—Medium in size, Orange Yellow (Plate No. 3) in color, medium in quantity.

*Filaments.*—Medium in length, Tyrian Rose (Plate No. 12) in color.

*Pollens.*—Medium in quantity, Orange Yellow (Plate No. 3) in color.

*Styles.*—Thin, uneven in height, Capucine Buff (Plate

No. 3) toward the base, Tyrian Rose (Plate No. 12) toward the upper end.

*Stigma.*—Medium in size, Tyrian Rose (Plate No. 12) on the under side of the rim, with a Martius Yellow (Plate No. 4) area close around the orifice.

*Ovaries.*—All enclosed.

*Hips.*—About four-fifths of an inch in diameter; orange yellow in color; shape of a well known Baldwin apple.

*(11) Disease resistance*

This new variety is more resistant to black spots and mildew than its parental varieties as indicated by outdoor garden tests conducted by the originator in Fairport, N. Y., in normal weather condition of the region, using the parental varieties for comparison.

I claim:

A new and distinct variety of hybrid tea rose plant belonging to the continuous or recurrent blooming variety of the cultivated species of the Genus Rosa, characterized as to novelty by its unusual hardiness, vigor and tall upright growth; by its large, leathery, glossy dark green leaves; by the distinctive Tyrian Rose (Plate No. 12), Capucine Buff (Plate No. 3) and amber colorings of its flowering buds; by the Rose Color (Plate No. 12), Capucine Buff and amber colorings of its blooms; by its sweet fragrance resembling that of a dish of slightly crushed red, ripe raspberries covered with amber colored honey; by its abundant production of blooms; and by its greater resistance to mildew and black spot infections than its parental varieties, substantially as hereinabove shown and described.

No references cited.